(12) United States Patent
Stevens et al.

(10) Patent No.: US 7,884,125 B2
(45) Date of Patent: Feb. 8, 2011

(54) STRAIGHTFORWARD ENTRY TO 7-AZABICYCLO[2.2.1]HEPTANE-1-CARBONITRILES AND SUBSEQUENT SYNTHESIS OF EPIBATIDINE ANALOGUES

(75) Inventors: Christian Stevens, Merelbeke (BE); Thomas Heugebaert, Reninge (BE)

(73) Assignee: Universiteit Gent, Ghent (BE)

( * ) Notice: Subject to any disclaimer, the term of this patent is extended or adjusted under 35 U.S.C. 154(b) by 172 days.

(21) Appl. No.: 12/188,524

(22) Filed: Aug. 8, 2008

(65) Prior Publication Data

US 2009/0275616 A1    Nov. 5, 2009

Related U.S. Application Data

(60) Provisional application No. 61/049,023, filed on Apr. 30, 2008.

(51) Int. Cl.
*A61K 31/403*    (2006.01)
*C07D 487/08*    (2006.01)

(52) U.S. Cl. .................. 514/413; 548/452; 548/465

(58) Field of Classification Search ............ 514/413; 548/452, 465
See application file for complete search history.

(56) References Cited

U.S. PATENT DOCUMENTS

| | | | |
|---|---|---|---|
| 5,510,490 A | 4/1996 | Pandey et al. | |
| 5,817,679 A | 10/1998 | Shen et al. | |
| 6,060,473 A | 5/2000 | Shen et al. | |
| 6,077,846 A | 6/2000 | Qian et al. | |
| 6,117,889 A | 9/2000 | Shen et al. | |
| 6,562,816 B2 | 5/2003 | Wishka et al. | |

FOREIGN PATENT DOCUMENTS

| | | |
|---|---|---|
| CA | 2 638 573 | 10/2009 |
| EP | 0 657 455 | 6/1995 |
| EP | 955301 | 11/1999 |
| WO | WO 00/23424 | 4/2000 |
| WO | WO 2007/137030 | 11/2007 |
| WO | WO -2007/137030 | * 11/2007 |

OTHER PUBLICATIONS

Dunlop et al., "In Vitro Screening Strategies for Nicotinic Receptor Ligands" *Biochemical Pharmacology* 74:1172-1181 (2007).
Grygorenko et al., "Stereoselective Synthesis of 2,4-methanoproline Homologues" *Tetrahedron: Asymmetry* 17:252-258 (2006).
Radchenko et al., "Conformationally Restricted Nonchiral Pipecolic Acid Analogues," *J. Org. Chem.* 74(15):5541-5544 (2009).
Search Report for British Patent Application No. GB 0919325.1, dated Mar. 1, 2010.

* cited by examiner

*Primary Examiner*—Susannah Chung
*Assistant Examiner*—Janet L Coppins
(74) *Attorney, Agent, or Firm*—Clark & Elbing LLP

(57) ABSTRACT

The present invention relates to a group of substituted-7-azabicyclo-[2.2.1]heptyl derivatives with biological activity. The present invention also relates to synthetic methods for producing said substituted-7-azabicyclo-[2.2.1]heptyl derivatives. The present invention also relates to certain intermediates for producing such substituted-7-azabicyclo-[2.2.1]heptyl derivatives, as well as a synthetic method for producing such intermediates. The present invention also relates to pharmaceutical compositions comprising such substituted-7-azabicyclo-[2.2.1]heptyl derivatives, as well as their use as medicaments for the treatment of diseases mediated by a Nicotinic Acetylcholine Receptor or a receptor being a member of the Neurotransmitter-gated Ion Channel Superfamily, such as pain, Alzheimer's disease, Parkinson's disease, schizophrenia, epilepsy and nicotine addiction.

32 Claims, No Drawings

STRAIGHTFORWARD ENTRY TO 7-AZABICYCLO[2.2.1]HEPTANE-1-CARBONITRILES AND SUBSEQUENT SYNTHESIS OF EPIBATIDINE ANALOGUES

CROSS REFERENCE TO RELATED APPLICATIONS

This application claims the benefit of the filing date of U.S. provisional patent application 61/049,023, filed Apr. 30, 2008, which is hereby is incorporated by reference in its entirety.

FIELD OF THE INVENTION

The present invention relates to a group of substituted-7-azabicyclo-[2.2.1]heptyl derivatives with biological activity. The present invention also relates to synthetic methods for producing substituted-7-azabicyclo-[2.2.1]heptyl derivatives belonging to this group. The present invention also relates to certain intermediates for producing such substituted-7-azabicyclo-[2.2.1]heptyl derivatives, as well as a synthetic method for producing such intermediates. The present invention also relates to pharmaceutical compositions comprising such substituted-7-azabicyclo-[2.2.1]heptyl derivatives, as well as their use as medicaments for the treatment of diseases mediated by a Nicotinic Acetylcholine Receptor or a receptor being a member of the Neurotransmitter-gated Ion Channel Superfamily, such as pain, Alzheimer's disease, Parkinson's disease, schizophrenia, epilepsy and nicotine addiction.

BACKGROUND OF THE INVENTION

The alkaloid epibatidine was first isolated in 1974 from the skin of the Ecuadorian frog *Epipedobates tricolor*. Shortly afterwards, its analgesic potency was shown to be about 200-fold higher than that of morphine. Regrettably however, the toxicity of epibatidine is too high for any human therapeutic use. The mode of action of epibatidine was later revealed as a highly potent nicotinic acetylcholine receptor agonist. This membrane bound pentameric ion channel has been associated with many neurological disorders such as Alzheimer disease, Parkinson disease and schizophrenia. For each of these disorders, there is a shift in the prevalence of the different nicotinic actylcholine receptor subtypes.

In order to improve the ratio of pharmacological to toxicological activity, many analogues have been synthesized. Most of them are substituted at position 2 of the 7-azabicyclo-[2.2.1]heptyl ring, e.g. WO 00/23424, U.S. Pat. Nos. 6,060,473, 5,817,679, 6,117,889, 6,077,846, 5,510,490, EP 657,455, U.S. Pat. No. 6,562,816, and EP 955,301. Grygorenko et al in Tetrahedron (2006) 17:252 has also disclosed one derivative substituted at position 1 of the 7-azabicyclo-[2.2.1]heptyl ring, i.e. 7-(1-phenylethyl)-7-azabicyclo-[2.2.1]heptyl-1-carbonitrile. However there is still a need in the art for more subtype selective epibatidine analogues in an effort to provide treatment for neurological diseases such as, but not limited to, Alzheimer disease, Parkinson disease and schizophrenia.

SUMMARY OF THE INVENTION

According to a first aspect, the present invention relates to a group of 1-substituted-7-azabicyclo[2.2.1]heptyl derivatives represented by the structural formula (I):

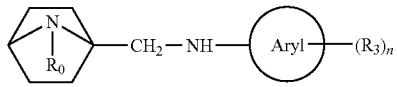

or the structural formula (II):

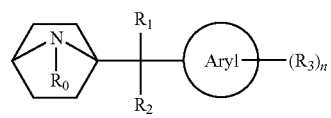

wherein:
  $R_0$ is selected from the group consisting of hydrogen, benzyl, naphthylmethyl, $C_{3-4}$ alkenyl and $C_{1-8}$ alkyl, wherein said benzyl is optionally substituted with one to three substituents independently selected from the group consisting of halogen, $C_{1-4}$ alkyl, $C_{1-4}$ alkoxy, trifluoromethyl, trifluoromethoxy, dimethylaminoethoxy, dimethylaminopropoxy, morpholinoethoxy, phenoxy, phenoxymethyl, heteroaryl and heteroarylmethyl;
  $R_1$ is hydrogen and $R_2$ is hydroxyl, or $R_1$ in combination with $R_2$ is oxo or imino;
  $R_3$ is a substituent selected from the group consisting of fluoro, chloro, bromo, $C_{1-4}$ alkyl, $C_{1-4}$ alkoxy, $C_{1-4}$ alkylthio, cyano, phenyl, trifluoromethyl, trifluoromethoxy, amino, dimethylamino and tert-butylcarboxylate; and
  n is 0, 1 or 2; and
  Aryl is an arylene or heteroarylene divalent group, or a pharmaceutically acceptable salt thereof, or an enantiomer, or a stereoisomeric form thereof, or a solvate thereof.

According to a second aspect, the present invention relates to a method for producing 1-substituted-7-azabicyclo[2.2.1] heptyl derivatives represented by the structural formula (I), a method for producing 1-substituted-7-azabicyclo[2.2.1]heptyl derivatives represented by the structural formula (II) wherein $R_1$ is hydrogen and $R_2$ is hydroxyl, and a method for producing 1-substituted-7-azabicyclo[2.2.1]heptyl derivatives represented by the structural formula (II) wherein $R_1$ in combination with $R_2$ is oxo.

According to a third aspect, the present invention relates to a group of 1-cyano-7-$R_0$-substituted-7-azabicyclo[2.2.1]-heptanes, wherein $R_0$ is selected from the group consisting of hydrogen, benzyl, naphthylmethyl, $C_{3-4}$ alkenyl and $C_{1-8}$ alkyl, wherein said benzyl is optionally substituted with one to three substituents independently selected from the group consisting of halogen, $C_{1-8}$ alkyl, $C_{1-8}$ alkoxy, trifluoromethyl, trifluoromethoxy, dimethylaminoethoxy, dimethylaminopropoxy, morpholinoethoxy, phenoxy, phenoxymethyl, heteroaryl and heteroaryl-methyl, a method for producing them, and their use as intermediates for producing the 1-substituted-7-azabicyclo[2.2.1]heptyl derivatives represented by the structural formulae (I) and (II).

According to a fourth aspect, the present invention relates to pharmaceutical compositions comprising a 1-substituted-7-azabicyclo[2.2.1]-heptyl derivative represented by the structural formula (I) or the structural formula (II). These pharmaceutical compositions are useful for use as medicaments for the treatment of diseases mediated by a Nicotinic Acetylcholine Receptor or a receptor being a member of the Neurotransmitter-gated Ion Channel Superfamily, such as pain, Alzheimer's disease, Parkinson's disease, schizophrenia, epilepsy and nicotine addiction.

DEFINITIONS

As used herein with respect to a substituting group, and unless otherwise stated, the term "$C_{1-4}$ alkyl" means straight and branched chain saturated acyclic hydrocarbon monovalent groups having from 1 to 4 carbon atoms such as, for example, methyl, ethyl, propyl, n-butyl, 1-methylethyl (isopropyl), 2-methylpropyl (isobutyl) and 1,1-dimethylethyl (ter-butyl). By analogy, the term "$C_{1-8}$ alkyl" refers to such radicals having from 1 to 8 carbon atoms, including 2-methylbutyl, n-pentyl, dimethylpropyl, n-hexyl, 2-methylpentyl, 3-methylpentyl, n-heptyl, n-octyl, and the like.

As used herein with respect to a substituting group, and unless otherwise stated, the term "aryl" designate any mono- or polycyclic aromatic monovalent hydrocarbon group having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_{4-8}$ cycloalkyl groups such as, for instance, indanyl, tetrahydronaphtyl, fluorenyl and the like, all of the said radicals being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein with respect to a substituting group, and unless otherwise stated, the term "$C_{1-4}$ alkoxy" refers to substituents wherein a carbon atom of a $C_{1-4}$ alkyl group (such as defined herein), is attached to an oxygen atom through a single bond such as, but not limited to, methoxy, ethoxy, propoxy, n-butoxy, pentoxy, isopropoxy, sec-butoxy, and tert-butoxy.

As used herein and unless otherwise stated, the term "stereoisomeric form" refers to all possible different isomeric as well as conformational forms which the compounds of this invention may exhibit, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a derivative of this invention with a suitable inorganic solvent (e.g. hydrates) or a suitable organic solvent such as, but not limited to, alcohols (thus forming almcoholates), ketones, esters, ethers, nitriles (e.g. acetonitrile) and the like.

As used herein, the term "Parkinson's disease" refers to a chronic progressive nervous disease characterised by neurodegeneration, especially degeneration of dopaminergic neurons. Symptoms include stooped posture, resting tremor, weakness of resting muscles, a shuffling gait, speech impediments, movement difficulties and an eventual slowing of mental processes and dementia.

As used herein with respect to a substituting group, and unless otherwise stated, the term "heteroaryl" refers to a mono- or polycyclic, aromatically unsaturated monovalent hydrocarbon radical having from 2 up to 15 carbon atoms and including one or more heteroatoms in one or more rings, each of said rings having from 3 to 10 atoms (and optionally further including one or more heteroatoms attached to one or more carbon atoms of said ring, for instance in the form of a carbonyl or thiocarbonyl or selenocarbonyl group, each of said heteroatoms being independently selected from the group consisting of nitrogen, oxygen and sulfur, also including radicals wherein a heterocyclic ring is fused to one or more aromatic hydrocarbon rings for instance in the form of benzo-fused, dibenzo-fused or naphtho-fused heterocyclic radicals; and also including radicals wherein each carbon atom of each ring may furthermore be independently substituted with a substituent selected from the group consisting of halogen, nitro, $C_{1-4}$ alkyl (optionally containing, in the main chain or a side chain, one or more atoms or groups such as oxo, hydroxyl, ether, thioether, acetal, amino, or halogen).

As used herein with respect to a substituting group, and unless otherwise stated, the term "arylene" designate a divalent hydrocarbon group derived from "aryl" by abstracting a hydrogen atom.

As used herein with respect to a substituting group, and unless otherwise stated, the term "heteroarylene" designate a divalent hydrocarbon group derived from "heteroaryl" by abstracting a hydrogen atom.

DETAILED DESCRIPTION OF THE INVENTION

The present invention relates to various groups of novel 1-substituted-7-azabicyclo[2.2.1]heptyl derivatives which have desirable biological properties such as binding to a Nicotinic Acetylcholine Receptor or a receptor being a member of the Neurotransmitter-gated Ion Channel Superfamily. Based on this activity, and the fact that these compounds are not toxic to human cells, these compounds are useful in the prevention and/or treatment of diseases mediated by a Nicotinic Acetylcholine Receptor or a receptor being a member of the Neurotransmitter-gated Ion Channel Superfamily such as, but not limited to, pain, Alzheimer's disease, Parkinson's disease, schizophrenia, epilepsy and nicotine addiction.

In the broadest expression, the class of novel biologically active 1-substituted-7-azabicyclo[2.2.1]heptyl derivatives according to the first aspect of this invention may be represented by the structural formula (I) or the structural formula (II), including stereoisomers, solvates and pharmaceutically acceptable salts thereof. This broad class may be sub-divided into several sub-classes wherein each substituent $R_0$ to $R_3$, and/or the divalent group (Aryl) may independently be defined in a more restricted manner, at will and independently from each other. Exemplary but non-limiting embodiments of such sub-classes may be defined as follows:

Aryl is phenylene, n is 1,

Aryl is pyrid-3-ylene or pyrid-2-ylene.

The derivatives represented by the above structural formula (I) or (II) may be in the form of a pharmaceutically acceptable salt. The latter include any therapeutically active non-toxic addition salt which compounds represented by the structural formula (I) or (II) are able to form with a salt-forming agent. Such addition salts may conveniently be obtained by treating the said derivative of the invention with an appropriate salt-forming acid or base. For instance, derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as but not limited to hydrohalides (e.g. hydrochloride and hydrobromide), sulfate, nitrate, phosphate, diphosphate, carbonate, bicarbonate, and the like; and organic monocarboxylic or dicarboxylic acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzenesulfonate, p-toluenesulfonate, salicylate, p-aminosalicylate, pamoate, bitartrate, camphorsulfonate, edetate, 1,2-ethanedisulfonate, fumarate, glucoheptonate, gluconate, glutamate, hexylresorcinate, hydroxynaphtoate, hydroxyethanesulfonate, mandelate, methylsulfate, pantothenate, stearate, as well as salts derived from ethanedioic, propanedioic, butanedioic, (Z)-2-butenedioic, (E)2-butenedioic, 2-hydroxybutanedioic, 2,3-dihydroxybutanedioic, 2-hydroxy-1,2,3-propanetricarboxylic and cyclohexanesulfamic acids and the like.

The derivatives of the structural formula (I) or (II) having acidic properties may be converted in a similar manner into the corresponding therapeutically active, non-toxic base addition salt form. Examples of appropriate salt-forming bases include, for instance, inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylenediamine, chloroprocaine, choline, diethanolamine, ethylenediamine, N-methylglucamine, procaine and the like.

Reaction conditions for treating the derivatives having the structural formula (I or II) of this invention with an appropriate salt-forming acid or base are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected so as to impart greater water-solubility, lower toxicity, greater stability and/or slower dissolution rate to the derivative of this invention.

According to a second aspect, the present invention relates to a method for producing 1-substituted-7-azabicyclo[2.2.1] heptyl derivatives represented by the structural formula (II) wherein $R_1$ is hydrogen and $R_2$ is hydroxyl, comprising reacting a 1-formyl-7-$R_0$-substituted-7-azabicyclo[2.2.1]-heptane, wherein $R_0$ is as defined in the structural formula (II), with an optionally substituted aryl iodide or aryl bromide represented by the structural formula Y-Aryl-$(R_3)_n$ wherein Y is iodo or bromo, Aryl, n and $R_3$ are as defined in the structural formula (II).

Representative examples of optionally substituted aryl iodides or aryl bromides, wherein Aryl is an arylene divalent group, suitable for this reaction include commercially available products such as, but not limited to:

non-substituted aryl iodides or aryl bromides, e.g. phenyl iodide and phenyl bromide;

mono-substituted aryl iodides or aryl bromides, e.g. 4-bromophenetole, 3-bromophenetole, 2-bromophenetole, 4-iodophenetole, 4-bromoanisole, 3-bromoanisole, 2-bromoanisole, 3-bromothioanisole, 2-bromothioanisole, 2-iodothioanisole, 3-iodothioanisole, 4-iodothioanisole, 4-n-butoxybromobenzene, 4-tert-butoxybromobenzene, 2-(trifluoromethoxy)bromo-benzene, 3-(trifluoromethoxy)bromobenzene, 4-(trifluoromethoxy)bromo-benzene, 2-(trifluoromethoxy)iodobenzene, 3-(trifluoromethoxy)iodo-benzene, 4-(trifluoromethoxy)iodobenzene, and 1-bromo-3-isopropoxybenzene; and poly-substituted aryl iodides or aryl bromides, e.g. 2,4-dibromoanisole, 2,6-dibromoanisole, 3,5-dibromoanisole, 4-bromo-3-methylanisole, 4-bromo-2-methylanisole, 1-bromo-3,5-dimethoxybenzene, 1-bromo-2,4-dimethoxybenzene, 1-bromo-2,4,6-trimethoxybenzene, 1-bromo-3,4,5-trimethoxybenzene, 4-bromo-2,6-dimethylanisole, 2,4,6-tribromoanisole, 3-bromo-4-chloroanisole, 4-bromo-3-chloroanisole, 2-bromo-3-fluoroanisole, 2-bromo-4-fluoroanisole, 2-bromo-5-fluoroanisole, 2-bromo-6-fluoroanisole, 3-bromo-4-fluoroanisole, 3-bromo-5-fluoroanisole, 4-bromo-2-fluoroanisole, 4-bromo-3-fluoroanisole, 3,5-dibromothioanisole and 1-bromo-3,4-dimethoxybenzene.

Representative examples of optionally substituted aryl iodides or aryl bromides, wherein Aryl is a heteroarylene divalent group, suitable for this reaction include commercially available products such as, but not limited to, 2,5-dibromopyridine, 2,6-dibromopyridine, 3,4-dibromopyridine, 3,5-dibromopyridine, 3-bromo-2-chloropyridine, 5-bromo-2-chloropyridine, 2-bromo-5-chloropyridine, 2-chloro-3,5-dibromopyridine, 2-fluoro-3,5-dibromo-pyridine, 5-bromo-2-fluoropyridine, 3,5-dibromo-2-iodopyridine, 2-bromo-6-methoxypyridine, 5-bromo-2-methoxypyridine, 2-bromo-6-ethoxypyridine, 2-bromo-3-methylpyridine, 3-bromo-4-methylpyridine, 2-bromo-4-methylpyridine, 2-bromo-5-methylpyridine, 6-bromo-2-picoline, 5-bromo-2-picoline, 2-bromo-4-ethyl-pyridine, 2-bromo-5-cyanopyridine, 5-bromonicotinitrile, 5-bromo-2-(dimethylamino)pyridine, 2-bromo-3-phenylpyridine, 2-bromo-4-phenylpyridine, 2-bromo-5-phenylpyridine, 2-bromo-6-phenylpyridine, 3-bromo-2-phenyl-pyridine, 3-bromo-4-phenylpyridine, 3-bromo-5-phenylpyridine, 4-bromo-3-phenylpyridine, 5-bromo-2-phenylpyridine, 2-bromo-5-(trifluoromethyl)pyridine, 2-bromo-6-(trifluoromethyl)pyridine, 3-bromo-5-(trifluoromethyl)pyridine, 5-bromo-2-(trifluoromethyl)pyridine, tert-butyl 5-bromopyridine-2-carboxylate, 2-amino-6-bromopyridine, 2-amino-3-bromopyridine, 2-amino-5-bromopyridine and 3-amino-6-bromopyridine.

According to a specific embodiment of the present invention, the above method for producing 1-substituted-7-azabicyclo[2.2.1]heptyl derivatives represented by the structural formula (II) wherein $R_1$ is hydrogen and $R_2$ is hydroxyl may start from a 1-formyl-7-$R_0$-substituted-7-azabicyclo[2.2.1]-heptane wherein $R_0$ is not hydrogen, i.e. wherein the substituent $R_0$ acts as a N-protecting group, in which case the method may further comprise a step of cleaving off the N-protecting $R_0$ substituent to produce a derivative represented by the structural formula (II) wherein $R_0$ is hydrogen.

According to another embodiment, the present invention relates to a method for producing 1-substituted-7-azabicyclo [2.2.1]heptyl derivatives represented by the structural formula (II), wherein $R_1$ in combination with $R_2$ is oxo, comprising reacting a 1-cyano-7-$R_0$-substituted-7-azabicyclo [2.2.1]-heptane, wherein $R_0$ is as defined in the structural formula (II), with an optionally substituted aryl iodide or aryl bromide represented by the structural formula Y-Aryl-$(R_3)_n$ wherein Y is iodo or bromo, Aryl, n and $R_3$ are as defined in the structural formula (II). Representative examples of optionally substituted aryl iodides or aryl bromides, wherein Aryl is an arylene or a heteroarylene divalent group, and being suitable for this reaction are as defined in details hereinabove.

According to a specific embodiment of the present invention, the above method for producing 1-substituted-7-azabicyclo[2.2.1]heptyl derivatives represented by the structural formula (II) wherein $R_1$ in combination with $R_2$ is oxo may start from a 1-cyano-7-$R_0$-substituted-7-azabicyclo[2.2.1]-heptane wherein $R_0$ is not hydrogen, i.e. wherein the substituent $R_0$ acts as a N-protecting group, in which case the method may further comprise a step of cleaving off the N-protecting $R_0$ substituent to produce a derivative represented by the structural formula (II) wherein $R_0$ is hydrogen.

According to another aspect, the present invention relates to a method for producing 1-substituted-7-azabicyclo[2.2.1] heptyl derivatives represented by the structural formula (I), comprising submitting a 1-aminomethyl-7-$R_0$-substituted-7-azabicyclo[2.2.1]-heptane, wherein $R_0$ is as defined in the structural formula (I), to a reaction step with an optionally substituted aryl iodide or aryl bromide represented by the structural formula Y-Aryl-$(R_3)_n$ wherein Y is iodo or bromo, Aryl, n and $R_3$ are as defined in the structural formula (I). Preferably, said reaction step is a Buchwald-Hartwig cross-coupling reaction. This type of reaction is well known to the person skilled in the art and may be performed in the presence of a catalytic amount of a palladium complex catalyst. Suitable examples of palladium complex catalysts for this purpose include complexes wherein palladium is coordinated with monodentate ligands selected from the group consisting of chloro and triarylphosphines (e.g. triphenylphosphine and tri-(o-tolyl)phosphine), and/or bidentate ligands such as, but not limited to:

2,2'-bis-(diphenylphosphino)-1,1'-binaphthyl (BINAP),
1,3-bis-(diphenylphosphino)-propane (DPPP),
1,1'-bis-(diphenylphosphino)-ferrocene (DPPF),
di-t-butyl-{1-[2-(dicyclohexylphosphanyl)ferrocenyl] ethyl}phosphine (DFEP), and
BINAP.

According to a specific embodiment of the present invention, the above method for producing 1-substituted-7-azabicyclo[2.2.1]heptyl derivatives represented by the structural formula (I) may start from a 1-cyano-7-$R_0$-substituted-7-azabicyclo[2.2.1]-heptane wherein $R_0$ is not hydrogen, i.e. wherein the substituent $R_0$ acts as a N-protecting group, in which case the method may further comprise a step of cleaving off the N-protecting $R_0$ substituent to produce a derivative represented by the structural formula (I) wherein $R_0$ is hydrogen.

For performing one of the above methods, it may first be necessary to produce 1-formyl-7-$R_0$-substituted-7-azabicyclo[2.2.1]-heptanes or 1-cyano-7-$R_0$-substituted-7-azabicyclo[2.2.1]-heptanes, wherein $R_0$ is selected from the group consisting of hydrogen, benzyl, naphthylmethyl, $C_{3-4}$ alkenyl and $C_{1-8}$ alkyl, and wherein said benzyl is optionally substituted with one to three substituents independently selected from the group consisting of halogen, $C_{1-8}$ alkyl, $C_{1-8}$ alkoxy, trifluoromethyl, trifluoromethoxy, dimethylaminoethoxy, dimethylaminopropoxy, morpholinoethoxy, phenoxy, phenoxymethyl, heteroaryl and heteroarylmethyl.

A non-limiting method for producing a 1-cyano-7-$R_0$-substituted-7-azabicyclo[2.2.1]-heptane comprises reacting 4-methanesulfonylcyclohexanone with a molar excess of a primary amine $R_0 NH_2$, wherein $R_0$ is selected from the group consisting of benzyl, naphthylmethyl, $C_{3-4}$ alkenyl and $C_{1-8}$ alkyl, and wherein said benzyl is optionally substituted with 1 to 3 substituents independently selected from the group consisting of halogen, $C_{1-4}$ alkyl, $C_{1-4}$ alkoxy, trifluoromethyl, trifluoromethoxy, dimethylaminoethoxy, dimethylaminopropoxy, morpholinoethoxy, phenoxy, phenoxymethyl, heteroaryl and heteroarylmethyl. Production of 4-methanesulfonylcyclohexanone itself is illustrated in a following example.

In order to suitably use a compound disclosed in this invention or a pharmaceutically acceptable salt, or solvate thereof, for the therapeutic treatment (including prophylactic treatment) of mammals including humans, it is usually formulated in accordance with standard pharmaceutical practice as a pharmaceutical composition including one or more appropriate pharmaceutically acceptable excipients.

The term "pharmaceutically acceptable carrier or excipient" as used herein in relation to pharmaceutical compositions and combined preparations means any material or substance with which the active principle, i.e. the derivative of the structural formula (I) or (II) may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents. may also be prepared by micronisation, for instance in view to obtain them in the form of microspheres usually having a diameter of about 1 to 10 µm, namely for the manufacture of microcapsules for controlled or sustained release of the biologically active ingredient(s).

Suitable surface-active agents to be used in the pharmaceutical compositions of the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidylcholine, dipalmitoylphoshatidylcholine and their mixtures.

Suitable non-ionic surfactants include polyethoxylated and poly-propoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediamino-polypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxy-polyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having four hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-$C_{1-4}$ alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active ingredient in the compositions of the present invention. Control release compositions may thus be achieved by selecting appropriate polymer carriers such as for example polyesters, polyaminoacids, polyvinyl-pyrrolidone, ethylene-vinyl acetate copolymers, methylcellulose, carboxy-methylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

In another aspect the present invention relates to a method of preventing or treating a disease, comprising the administration of a therapeutically effective amount of a derivative as defined in any specific embodiment above, in particular being represented by any of the structural formulae (I) and (II), to a patient in need thereof, optionally in combination with one or more pharmaceutically acceptable carriers. In particular the 1-substituted-7-azabicyclo[2.2.1]heptyl derivatives described herein are useful in modulating cholinergic function. Numerous diseases, especially those mediated by a Nicotinic Acetylcholine Receptor or a receptor being a member of the Neurotransmitter-gated Ion Channel Superfamily, may be treated by means of a 1-substituted-7-azabicyclo [2.2.1]heptyl derivative such as disclosed herein.

Non-limiting examples of such diseases include various forms of the inflammatory bowel disease (including, but not limited to, ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amylotropic lateral sclerosis, cognitive dysfunction, hypertension, bulimia, anorexia, obesity, cardiac arrythmia, gastric acid hypersecretion, ulcers, pheochromocytoma, progressive supramuscular palsy, chemical dependencies and addictions (e.g. dependencies on, or addictions to, nicotine (and/or tobacco products), alcohol, benzodiazepines, barbiturates, opioids or cocaine), headache, stroke, traumatic brain injury, obsessive-compulsive disorders, psychosis, Huntington's Chorea, tardive dyskinesia, hyperkinesia, dyslexia, schizophrenia, multi-infarct dementia, age-related cognitive decline, epilepsy, senile dementia of the Alzheimer's type, Parkinson's disease, attention deficit hyperactivity disorder (ADHD) and Tourette's Syndrome.

The compounds of this invention may also be used in combination with:
- one or more antidepressant drugs such as, but not limited to, tricyclic antidepressants and serotonin re-uptake inhibiting antidepressants, in order to treat both the cognitive decline and depression associated with Alzheimer's Disease, Parkinson Disease, or traumatic brain injury;
- one or more muscarinic agonists in order to stimulate both central muscarinic and nicotinic receptors for the treatment, for example, of cognitive dysfunction, age-related cognitive decline, Alzheimer's Disease, Parkinson Disease, stroke or Huntington's Chorea;
- one or more neurotrophic factors such as NGF in order to maximize cholinergic enhancement for the treatment, for example, cognitive dysfunction, age related cognitive decline, Alzheimer's Disease, Parkinson Disease, stroke or Huntington's Chorea;
- one or more agents that slow or arrest Alzheimer's Disease such as, but not limited to, cognition enhancers, amyloid aggregation inhibitors, secretase inhibitors, tau kinase inhibitors, neuronal anti-inflammatory agents and estrogen-like therapeutic agents.

The precise biological activity profile of the 1-substituted-7-azabicyclo[2.2.1]heptyl derivatives disclosed in this invention may be determined by using one or more of the assays described in the review article published by Dunlop et al in *Biochemical Pharmacology* (2007) 74:1172-1181 such as, but not limited to:
- assays using a cell system wherein the alfa7-subunit of the Nicotinic Acetylcholine Receptor complex is heterologously expressed, e.g. Xenopus (frog) oocytes or GH4C1 (mammalian) cells;
- a radioactive displacement binding assay, e.g. using 3H labelled epibatidine and the Xenopus oocyte expression system;
- a functional cell based binding assay (e.g. the Ca2+ flux FLIPR assay) wherein (Xenopus/GH4C1) a ligand gated ion channel consisting out of 5 alfa7-subunits (pentamer) is formed in a cell system; in such assays, binding of a ligand causes ion fluxes which can be measured using fluorescent labelled ions e.g. through the "Fluorescent Imaging Plate Reading (FLIPR)" technique; this approach provides, next to the fact that a ligand binds to a receptor, also information with respect to the receptor activity.
- electrophysiological recording such as the Two Electrode Voltage Clamp technique (TEVC), e.g. used with the radioligand binding assay and the Xenopus cell system, or the Patch Clamp technique, e.g. in combination with the "U-tube bathing technique".

In order to suitably use the 1-substituted-7-azabicyclo [2.2.1]heptyl derivatives disclosed in this invention for therapeutic or prophylactic purpose, such compounds are preferably administered in a therapeutically effective amount (e.g. an analgesic dose when the pathologic condition to be treated is pain), e.g. a daily dose in the range of, for example, 0.1 mg to 75 mg per kg body weight is received, said daily dose being given if required in divided sub-doses, also depending upon the patient to be treated and the severity of the disease to be cured. In general, lower doses will be administered when a parenteral route is employed. Thus, for example, for intravenous administration, a dose in the range of, for example, 0.5 mg to 30 mg per kg body weight will preferably be used. Similarly, for administration by inhalation, a dose in the range of, for example, 0.5 mg to 25 mg per kg body weight will preferably be used. According to a particular embodiment, the envisaged administration route for the compounds of the invention is oral administration, particularly in tablet form. Typically, unit dosage forms will contain about 1 mg to 500 mg of a compound of this invention.

The following examples are merely illustrative of the production and characterization of some 1-substituted-7-azabicyclo[2.2.1]heptyl derivatives of the present invention, but any type of compounds represented by the structural formulae (I) or (II) may be produced in accordance with the synthetic procedures described herein.

EXAMPLE 1

Synthesis of 4-methanesulfonylcyclohexanone

Synthesis proceeds as shown in scheme 1. Starting from the commercially available protected cyclohexanone 6, the keto function was reduced with lithium aluminium hydride, followed by the activation of the hydroxyl function as the corresponding mesylate. After deprotection of the acetal 8, the desired precursor was obtained.

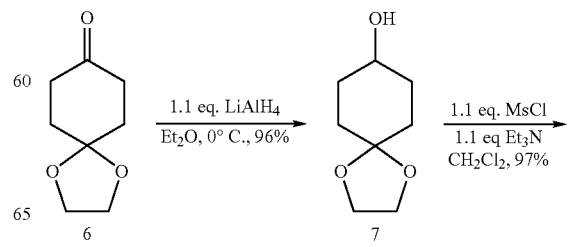

Scheme 1

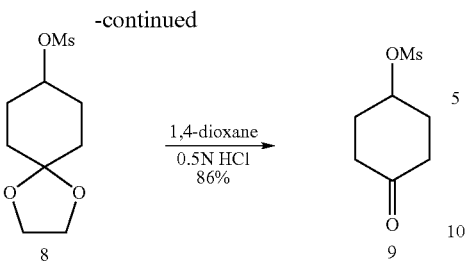

Details of these three steps are as follows:

Synthesis of Compound 7
(1,4-dioxaspiro[4.5]denan-8-ol)

In a dry 250 ml flask 2.5 g (68.5 mmole, 1 eq.) LiAlH$_4$ was suspended in 20 ml dry diethyl ether. The flask was placed under inert N$_2$-atmosphere and cooled to 0° C. 10.4 g (66.6 mmole, 1 eq.) 1,4-dioxaspiro[4.5]decan-8-one 6 was dissolved in 100 ml dry diethyl ether and slowly added to the suspension. The reaction mixture was stirred for 30 minutes at room temperature. Water, diluted with THF, was added in order to remove the excess LiAlH$_4$. The reaction mixture was filtrated over MgSO$_4$ and the volatile components were removed by evaporation.

Synthesis of Compound 8
(8-methanesulfonyl-1,4-dioxaspirondecane)

In a 250 ml flask 10.36 g (65.5 mmole, 1 eq.) 1,4-dioxaspiro[4.5]denan-8-ol 7 and 7.31 g (72.2 mmole, 1.1 eq.) triethylamine were dissolved in 80 ml CH$_2$Cl$_2$. The flask was cooled to 0° C. and a solution of 8.27 g (72.2 mmol, 1.1 eq.) methanesulfonyl chloride in 20 ml CH$_2$Cl$_2$ was slowly added. Afterwards the cooling system was removed and the reaction mixture was left under agitation for 24 hours. Triethylamine hydrochloride crystals precipitated during this period. 200 ml saturated NaHCO$_3$ solution was added and compound 8 was extracted three times with dichloromethane. The combined organic phases were dried over MgSO$_4$, solids were filtered off and the volatile components were evaporated.

Synthesis of Compound 9
(4-methanesulfonylcyclohexanone)

15.36 grams (65 mmole) of 8-methanesulfonyl-1,4-dioxaspirondecane 8 was dissolved in 300 ml 1,4-dioxane and added to 300 ml 0.5M HCl. After stirring for 48 hours the pH was set to 8 using a 2M solution of KOH. The reaction mixture was extracted three times with CH$_2$Cl$_2$. The combined extracts were washed 4 times with a saturated NaHCO$_3$ solution and dried over MgSO$_4$. After filtration of the solids and evaporation of the volatile components, compound 9 was obtained as a slightly yellow solid.

EXAMPLE 2

Synthesis of 7-R-substituted-7-azabicyclo[2.2.1] heptyl-1-carbonitriles

The key step involves the one-pot procedure of imine formation, addition of cyanide to the imine function, followed by intramolecular nucleophilic substitution, as shown in scheme 2. This was performed by treating the mesyloxyketone 9 with three equivalents of amine (one equivalent is needed to trap the methylsulfonic acid after ring closure) and two equivalents of acetone cyanohydrine, the cyanide source, in a closed vessel in methanol for two days. The conversion of the mesyloxyketone 9 to the 7-azabicyclo[2.2.1]hexane-1-carbonitrile 10 was complete, however the purification of the resulting compound by flash chromatography (or by crystallization of the hydrochloride salt in case of compound 10a) lowers the reaction yield. Compounds 10 exhibit a high affinity for silica gel, leading to some product loss during purification. Six illustrative substituted 7-azabicyclo[2.2.1]heptane-1-carbonitriles were obtained. This method proves to be superior to the method of Grygorenko et al (cited supra) since no evidence of isomer formation could be found.

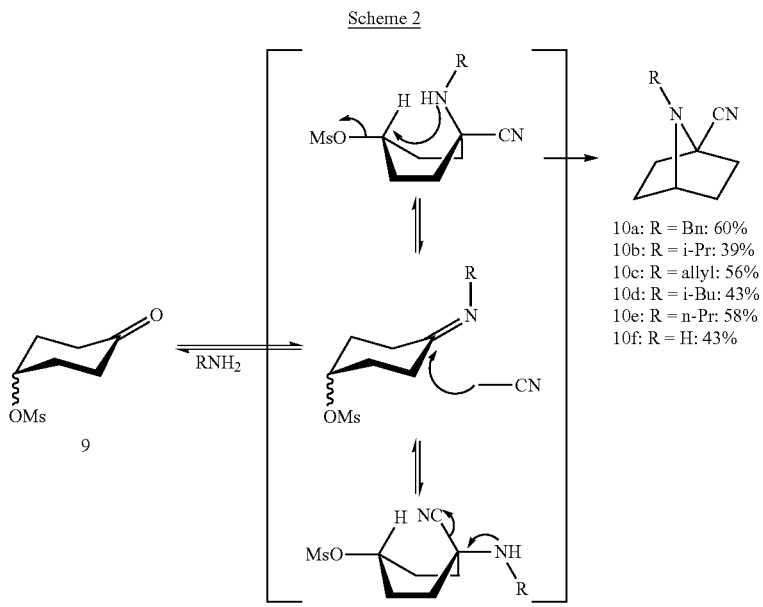

Scheme 2

10a: R = Bn: 60%
10b: R = i-Pr: 39%
10c: R = allyl: 56%
10d: R = i-Bu: 43%
10e: R = n-Pr: 58%
10f: R = H: 43%

Details of these syntheses are as follows:

Synthesis of Compound 10a
(7-benzyl-7azabicyclo[2.2.1]heptyl-1-carbonitrile

In a dry, pressure resistant vessel of 20 ml, 1.25 g (6.5 mmole, 1 eq.) 4-methanesulfonylcyclohexanone 9, 0.70 g (6.5 mmole, 1 eq.) benzylamine, 1.11 g (13 mmole, 2 eq.) acetone cyanohydrine and 1.32 g (13 mmole, 2 eq.) triethylamine were dissolved in 16 ml dry methanol. The vessel was closed and heated to 100° C. for 50 hours. Methanol was evaporated and the residue was re-dissolved in dichloromethane. The solution was washed with a saturated $NaHCO_3$ solution and dried over $MgSO_4$. After filtration of the solids the volatile components were evaporated. Chromatography yields 60% 7-benzyl-7azabicyclo[2.2.1]heptyl-1-carbonitrile 10a as a yellow oil which was characterised as follows:

$^1$H-NMR (300 MHz, $CDCl_3$) (ppm): 1.33-1.44 (2H, m, 2×C$\underline{H}_a$H$_b$CH); 1.77-1.95 (4H, m, 2×CH$_a\underline{H}_b$CH, 2×C$\underline{H}_a$H$_b$C$_q$); 2.09-2.22 (2H, m, 2×CH$_a\underline{H}_b$C$_q$); 3.26 (1H, t, J=4.4 Hz, $CH_2$C$\underline{H}$CH$_2$); 3.64 (2H, s, NC$\underline{H}_2$Ph); and 7.22-7.40 (5H, m, 5×C$\underline{H}$, Ph.);

$^{13}$C-NMR (75 MHz, $CDCl_3$) (ppm): 27.96 (2×$\underline{C}H_2$CH); 34.37 (2×$\underline{C}H_2$C$_q$); 50.38 (N$\underline{C}H_2$Ph); 58.43 ($CH_2$$\underline{C}$HCH$_2$); 59.53 (N—$\underline{C}_q$); 120.33 ($\underline{C}$≡N); 127.23 ($\underline{C}$H, Ph.); 128.36 ($\underline{C}$H, Ph.); 128.67 ($\underline{C}$H, Ph.); and 138.74 ($\underline{C}_q$, Ph.);

IR (cm$^{-1}$): 2240 (C≡N); and

MS$^{ES}$ m/z (%): 213 (M+H$^+$, 100); 91 (15).

Synthesis of Compounds 10b-f

In a dry, pressure resistant vessel of 20 ml, 1.25 g (6.5 mmole, 1 eq.) 4-methanesulfonylcyclohexanone 9, 19.5 mmole (3 eq.) amine and 1.11 g (13 mmole, 2 eq.) acetone cyanohydrine were dissolved in 16 ml dry methanol. The vessel was closed and heated to 100° C. for 50 hours. Methanol was evaporated and the residue was re-dissolved in dichloromethane. The solution was washed with a saturated $NaHCO_3$ solution and dried over $MgSO_4$. After filtration of the solids the volatile components were evaporated. Chromatography yields 7-azabicyclo[2.2.1]heptyl-1-carbonitriles 10b-f which were characterised by their spectral data as follows:

Compound 10b (Yield 39%)

$^1$H-NMR (300 MHz, $CDCl_3$) (ppm): 1.24 (6H, d, J=6.3 Hz, 2×C$\underline{H}_3$); 1.34-1.47 (2H, m, 2×C$\underline{H}_a$H$_b$CH); 1.75-1.91 (4H, m, 2×CH$_a\underline{H}_b$CH, 2×C$\underline{H}_a$H$_b$C$_q$); 2.09-2.21 (2H, m, 2×CH$_a\underline{H}_b$C$_q$); 2.68 (1H, septet, J=6.3 Hz, $CH_3$C$\underline{H}$CH$_3$); and 3.62 (1H, t, J=4.4 Hz, $CH_2$C$\underline{H}$CH$_2$);

$^{13}$C-NMR (75 MHz, $CDCl_3$) (ppm): 23.07 (2×$CH_3$); 28.17 (2×$CH_2$CH); 35.22 (2×$\underline{C}H_2$C$_q$); 46.54 ($CH_3\underline{C}$HCH$_3$); 57.09 (N—$\underline{C}_q$); 59.00 ($CH_2\underline{C}$HCH$_2$); and 121.78 ($\underline{C}$≡N);

IR (cm$^{-1}$): 2238 (C≡N); and

MS$^{IE}$ m/z (%): 164 (M$^+$, 16); 149 (57); 108 (8); 94 (100) and 67(10).

Compound 10c (Yield 56%)

$^1$H-NMR (300 MHz, $CDCl_3$) (ppm): 1.25-1.50 (2H, m, 2×C$\underline{H}_a$H$_b$CH); 1.77-1.93 (4H, m, 2×CH$_a\underline{H}_b$CH, 2×C$\underline{H}_a$H$_b$C$_q$); 2.04-2.16 (2H, m, 2×CH$_a\underline{H}_b$C$_q$); 3.14 (2H, br. d, J=5.8 Hz, NC$\underline{H}_2$); 3.47 (1H, t, J=4.5 Hz, $CH_2$C$\underline{H}$CH$_2$); 5.12-5.30 (2H, m, CH=C$\underline{H}_2$); and 5.92 (1H, dxdxt, J$_1$=17.2 Hz, J$_2$=10.1 Hz, J$_3$=6.3 Hz, C$\underline{H}$=CH$_2$);

$^{13}$C-NMR (75 MHz, $CDCl_3$) (ppm): 27.98 (2×$\underline{C}H_2$CH); 34.23 (2×$\underline{C}H_2$C$_q$); 49.42 (N$\underline{C}H_2$); 58.61 ($CH_2\underline{C}$HCH$_2$); 59.21 ($CH_2\underline{C}_q$CH$_2$); 117.47 (CH=$\underline{C}H_2$); 120.18 ($\underline{C}$≡N); and 135.21 ($\underline{C}$H=CH$_2$);

IR (cm$^{-1}$): 2240 (C≡N) and 1644 (C=C);

MS$^{ES}$ m/z (%): 163 (M+H$^+$, 100) and 136 (12).

Compound 10d (Yield 43%)

$^1$H-NMR (300 MHz, $CDCl_3$) (ppm): 0.95 (6H, d, J=6.6 Hz, 2×C$\underline{H}_3$); 1.35-1.42 (2H, m, 2×C$\underline{H}_a$H$_b$CH); 1.63-1.91 (5H, m, 2×CH$_a\underline{H}_b$CH, 2×C$\underline{H}_a$H$_b$C$_q$, NCH$_2$C$\underline{H}$(CH$_3$)$_2$); 1.99-2.09 (2H, m, 2×CH$_a\underline{H}_b$C$_q$); 2.24 (2H, d, J=7.2 Hz, NC$\underline{H}_2$CH(CH$_3$)$_2$); and 3.40 (1H, t, J=4.4 Hz, $CH_2$C$\underline{H}$CH$_2$);

$^{13}$C-NMR (75 MHz, $CDCl_3$) (ppm): 20.87 (2×$\underline{C}H_3$); 28.20 (2×$\underline{C}H_2$CH); 28.34 (NCH$_2\underline{C}$H(CH$_3$)$_2$); 34.35 (2×$\underline{C}H_2$C$_q$); 53.97 (N$\underline{C}H_2$CH(CH$_3$)$_2$); 59.65 ($CH_2\underline{C}$HCH$_2$); 59.92 (N$\underline{C}_q$); and 120.80 ($\underline{C}$≡N);

IR (cm$^{-1}$): 2241 (C≡N); and

MS$^{ES}$ m/z (%): 180 (M$^+$+2, 10) and 179 (M$^+$+1, 84).

Compound 10e (Yield 58%)

$^1$H-NMR (300 MHz, $CDCl_3$) (ppm): 0.96 (3H, t, J=7.4 Hz, C$\underline{H}_3$); 1.38-1.46 (2H, m, 2×C$\underline{H}_a$H$_b$CH); 1.56 (2H, sextet, J=7.4 Hz, C$\underline{H}_2$CH$_3$); 1.73-1.93 (4H, m, 2×CH$_a\underline{H}_b$CH, 2×C$\underline{H}_a$H$_b$C$_q$); 2.02-2.18 (2H, m, 2×CH$_a\underline{H}_b$C$_q$); 2.44 (2H, t, J=7.7 Hz, NC$\underline{H}_2$) and 3.48 (1H, t, J=4.4 Hz, $CH_2$C$\underline{H}$CH$_2$);

$^{13}$C-NMR (75 MHz, $CDCl_3$) (ppm): 11.99 ($\underline{C}H_3$); 22.55 ($\underline{C}H_2$CH$_3$); 28.09 (2×$\underline{C}H_2$CH); 34.20 (2×$\underline{C}H_2$C$_q$); 48.13 (N$\underline{C}H_2$); 58.89 ($CH_2\underline{C}$HCH$_2$); 59.67 (N$\underline{C}_q$) and 120.53 ($\underline{C}$≡N);

IR (cm$^{-1}$): 2241 (C≡N); and

MS$^{ES}$ m/z (%): 166 (M$^+$+2, 17); 165 (M$^+$+1, 100); 138 (7).

Compound 10f (Yield 43%)

$^1$H-NMR (300 MHz, $CDCl_3$) (ppm): 1.22-2.01 (8H, m, 4×C$\underline{H}_a$H$_b$, 4×CH$_a\underline{H}_b$); and 3.78 (1H, t, J=4.4 Hz, $CH_2$C$\underline{H}$CH$_2$);

$^{13}$C-NMR (75 MHz, $CDCl_3$) (ppm): 30.59 (2×$\underline{C}H_2$CH); 35.71 (2×$\underline{C}H_2$C$_q$); 55.43 (N$\underline{C}_q$); 57.46 ($CH_2\underline{C}$HCH$_2$) and 121.07 ($\underline{C}$≡N);

IR (cm$^{-1}$): 3207; 2243 (C≡N); and

MS$^{ES}$ m/z (%): 123 (M$^+$+1, 98); 106 (7).

EXAMPLE 3

Preparation of 1-substituted-7-benzyl-7-azabicyclo[2.2.1]heptyl Derivatives

In a first step, compound 10a (7-benzyl-7azabicyclo[2.2.1]heptyl-1-carbonitrile) was submitted to a partial reduction as shown in scheme 3 below, followed by acidic hydrolysis. Infrared analysis confirmed the reduction to the expected aldimine which however was quite resistant to hydrolysis, chromatography being needed to obtain the pure aldehyde 11 in 49% yield. The subsequent addition of the 2-chloropyridyl group provided the alcohol 12 in 91% yield.

Alternatively, the nucleophilic addition of the 2-chloropyridyl group was also performed directly onto the nitrile compound 10a. After acidic hydrolysis of the resulting imine, the ketone 13 was obtained in 73% yield.

Scheme 3

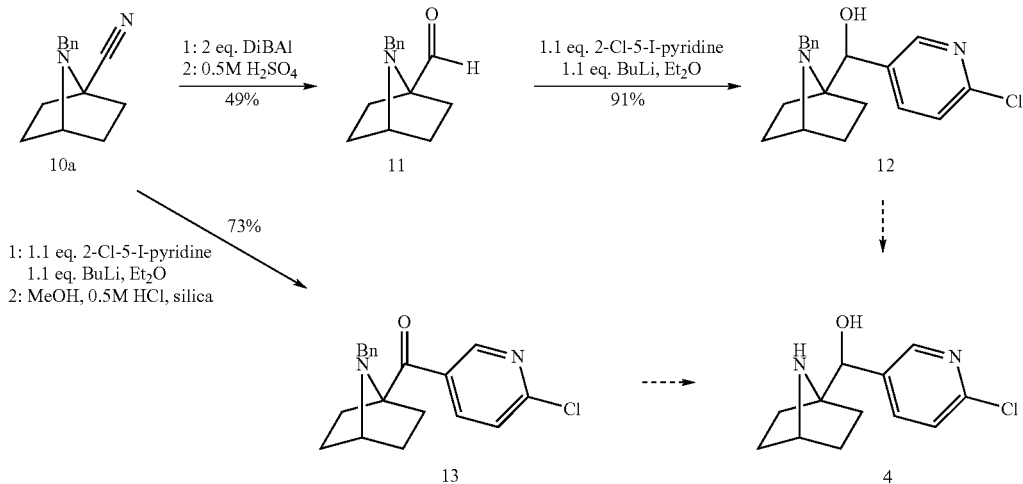

Synthesis of Compound 11 (7-benzyl-7-azabicyclo[2.2.1]heptyl-1-carbaldehyde)

In a dry 100 ml flask 0.7 g (3.3 mmole, 1 eq.) 7-benzyl-7-azabicyclo[2.2.1]heptyl-1-carbonitrile was dissolved in 35 ml dry diethyl ether. The flask was placed under inert $N_2$-atmosphere and cooled to −78° C. With a syringe 6.6 ml of a 1M solution of DiBAl (6.6 mmole, 2 eq.) was added. The reaction mixture was stirred for one hour at −78° C. and 5 hours at 20° C. 0.49 g (6.6 mmole, 2 eq.) ethyl formate was added. After 30 minutes stirring, 40 ml 0.5M $H_2SO_4$ was added, which was neutralised by means of 3M NaOH after 15 hours. The reaction mixture was extracted three times with diethyl ether and the combined organic phases were dried over $MgSO_4$. After filtration of the solids and removal of the volatile components, the resulting product (yield: 49%) was characterised by spectral data as follows:

$^1$H-NMR (300 MHz, $CDCl_3$) (ppm): 1.39-1.59 (4H, m, 2×$CH_{exo}\underline{H}_{endo}CH$, 2×$C\underline{H}_aH_bC_q$); 1.88-2.12 (4H, m, 2×$C\underline{H}_{exo}H_{endo}CH$, 2×$CH_a\underline{H}_bC_q$); 3.38 (1H, t, J=4.5 Hz, $CH_2C\underline{H}CH_2$); 3.51 (2H, s, $NC\underline{H}_2Ph$); 7.22-7.39 (5H, m, 5×$C\underline{H}$, Ph.) and 9.70 (1H, s, $CO\underline{H}$);
$^{13}$C-NMR (75 MHz, $CDCl_3$) (ppm): 28.46 (2×$\underline{C}H_2CH$); 29.84 (2×$\underline{C}H_2C_q$); 51.04 ($N\underline{C}H_2Ph$); 60.97 ($CH_2\underline{C}HCH_2$ ring); 76.14 ($CH_2\underline{C}_qCH_2$ ring); 127.31 ($\underline{C}H$, Ph.); 128.43 (2×$\underline{C}H$, Ph.); 128.98 (2×$\underline{C}H$, Ph.); 139.44 ($\underline{C}q$, Ph.) and 202.85 ($\underline{C}$=O);
IR ($cm^{-1}$): 1722 (C=O); and
$MS^{ES}$ m/z (%): 234 ($M+H_3O^+$, 38) and 216 ($M+H^+$, 100).

Synthesis of Compound 12

In a dry 50 ml flask 1.1 g (4.6 mmole, 1.1 eq.) 2-chloro-5-iodopyridine was dissolved in 30 ml dry diethyl ether. The flask was placed under inert $N_2$-atmosphere and cooled to −78° C. To this solution 1.84 ml of a 2.5M solution (4.6 mmol, 1.1 eq.) of BuLi was added. After stirring 2.5 hours at −78° C. a solution of 0.90 g (4.2 mmole, 1 eq.) 7-benzyl-7-azabicyclo[2.2.1]heptyl-1-carbaldehyde 11 in 10 ml dry diethyl ether was added. 30 minutes later the reaction mixture was allowed to heat up to 20° C. and left under agitation overnight. Methanol was added in order to neutralise the excess BuLi and the volatile components were evaporated. The reaction mixture was re-dissolved in a minimal amount of dry diethyl ether. The volatile components were evaporated and the precipitated salts were filtered off (yield 91%) and characterised by spectral data as follows:

$^1$H-NMR (300 MHz, $CDCl_3$) (ppm): 0.82-0.95 (1H, m, $C_qC\underline{H}_aH_bC_bH_2$); 1.15-1.25 (2H, m, 1×$CHC_b\underline{H}_{exo}\underline{H}_{endo}$, 1×$C_qC\underline{H}_aH_bC_aH_2$); 1.43-1.52 (1H, m, 1×$CHC_aH_{exo}\underline{H}_{endo}$); 1.56-1.65 (1H, m, 1×$CHC_b\underline{H}_{exo}H_{endo}$); 1.80 (1H, txt, $J_1$=12.1 Hz, $J_2$=3.9 Hz, $C_qCH_a\underline{H}_bC_aH_2$); 1.96 (1H, txt, $J_1$=12.1 Hz, $J_2$=3.9 Hz, $C_qCH_a\underline{H}_bC_bH_2$); 2.02-2.16 (1H, m, 1×$CHC_a\underline{H}_{exo}H_{endo}$); 3.25 (1H, t, J=4.7 Hz, $CH_2C\underline{H}CH_2$); 3.40 (1H, d, J=13.2 Hz, $NC\underline{H}_aH_bPh$); 3.61 (1H, br. s, OH); 3.85 (1H, d, J=13.2 Hz, $NCH_a\underline{H}_bPh$); 4.99 (1H, s, $C\underline{H}OH$); 7.23-7.44 (5H, m, 5×$C\underline{H}$ Ph.); 7.29 (1H, d, J=8.3 Hz, $C_qCHC\underline{H}$ pyr.); 7.73 (1H, dxd, $J_1$=8.3 Hz, $J_2$=2.4 Hz, $C_qC\underline{H}CH$ pyr.) and 8.36 (1H, d, J=2.4 Hz, $C_qC\underline{H}N$ pyr.);
$^{13}$C-NMR (75 MHz, $CDCl_3$) (ppm): 28.13 ($\underline{C}_bH_2CH_2$); 28.58 ($\underline{C}_bH_2CH_2$); 28.71 ($\underline{C}_aH_2CH_2$); 29.78 ($C_aH_2\underline{C}H_2$); 48.88 ($N\underline{C}H_2Ph$); 60.17 ($CH_2\underline{C}HCH_2$); 70.98 ($\underline{C}HOH$); 72.78 ($CH_2\underline{C}_qCH_2$); 123.83 ($C_q CHC\underline{H}$ pyr.); 127.28 (1×$\underline{C}H$, Ph.); 128.63 (4×$\underline{C}H$, Ph.); 135.77 ($\underline{C}_q$ pyr.); 137.41 ($C_q\underline{C}HCH$ pyr.); 139.47 ($\underline{C}_q$ Ph.); 148.16 ($C_q\underline{C}HN$ pyr.) and 150.49 ($\underline{C}_qCl$, pyr.);
IR ($cm^{-1}$): 3370 (OH);
$MS^{ES}$ m/z (%): 331 ($M+H^+$, 34); 329 ($M+H^+$, 100) and 274 (30).

Synthesis of Compound 13

In a dry 50 ml flask 1.1 g (4.6 mmole, 1.1 eq.) 2-chloro-5-iodopyridine was dissolved in 30 ml dry diethyl ether. The flask was placed under inert $N_2$-atmosphere and cooled to −78° C. To this solution 1.84 ml of a 2.5M solution (4.6 mmole, 1.1 eq.) of BuLi was added. After stirring 2.5 hours at −78° C. a solution of 0.89 g (4.2 mmole, 1 eq.) 7-benzyl-7-azabicyclo[2.2.1]heptyl-1-carbonitrile in 10 ml dry diethyl ether is added. 30 minutes later the reaction mixture was allowed to heat up to 20° C. and left under agitation overnight. Methanol was added in order to neutralise the excess BuLi and the volatile components were evaporated. The reaction mixture was re-dissolved in 40 ml of a 1:1 mixture of methanol and 0.5M HCl. 0.5 g silica gel was added and the mixture was stirred for 24 hours at 20° C. The pH was adjusted to 8 by adding a concentrated NaHCO$_3$ solution. Compound 13 was extracted three times by means of dichloromethane and the combined organic phases were dried over MgSO$_4$. After filtration of the solids and evaporation of the volatile components, compound 13 (yield 73%) was further purified by crystallisation from methanol and was characterised by spectral data as follows:

$^1$H-NMR (300 MHz, CDCl$_3$) (ppm): 1.49 (2H, dxdxd, $J_1$=11.6 Hz, $J_2$=9.3 Hz, $J_3$=4.1 Hz, 2×CHCH$_{exo}$H$_{endo}$ of 2×C$_q$CH$_a$H$_b$); 1.65-1.85 (2H, br. s, 2×CHCH$_{exo}$H$_{endo}$ of 2×C$_q$CH$_a$H$_b$); 1.89-2.08 (2H, m, 2×CHCH$_{exo}$H$_{endo}$); 2.20-2.46 (2H, br. s, 2×CHCH$_{exo}$H$_{endo}$ of 2×C$_q$CH$_a$H$_b$); 3.39 (2H, s, NCH$_2$Ph); 3.42 (1H, t, J=4.7 Hz, CH$_2$CHCH$_2$); 7.17-7.33 (5H, m, Ph.); 7.40 (1H, d, J=8.3 Hz, C$_q$CHCH pyr.); 8.71 (1H, dxd, $J_1$=8.3 Hz, $J_2$=2.3 Hz, C$_q$CHCH pyr.); 9.73 (1H, d, J=2.3 Hz, CHN, Pyr.);

$^{13}$C-NMR (75 MHz, CDCl$_3$) (ppm): 25.7-30.1 (4×CH$_2$ ring); 50.06 (NCH$_2$Ph); 59.86 (CH$_2$CHCH$_2$); 77.56 (CH$_2$C$_q$CH$_2$); 124.21 (C$_q$CHCH pyr.); 127.27 (1×CH Ph.); 128.48 (2×CH Ph.); 128.60 (2×CH Ph.); 129.47 (C$_q$, pyr.); 138.89 (C$_q$, Ph.); 139.93 (C$_q$CHCH pyr.); 152.34 (CHN pyr.); 155.44 (C$_q$Cl, pyr.) and 199.50 (CO);

IR (cm$^{-1}$): 1675 (C=O);

MS$^{ES}$ m/z (%): 329 (M+H$^+$, 41); 327 (M+H$^+$, 100); 323 (45) and 272 (80).

EXAMPLE 4

Preparation and Derivatisation of 7-benzyl-7-azabicyclo[2.2.1]hept-1-yl)(Pyridin-3-yl)methanone 14 ketone 14 was synthesized from 7-azabicyclo[2.2.1]heptane-1-carbonitrile 10a in 48% yield as shown in scheme 4. Then, refluxing ketone 14 with ammonium formate in the presence of Pd/C led to the complete removal of the benzyl group within 4 hours and compound 15 was recovered after crystallisation from diethyl ether.

Scheme 4

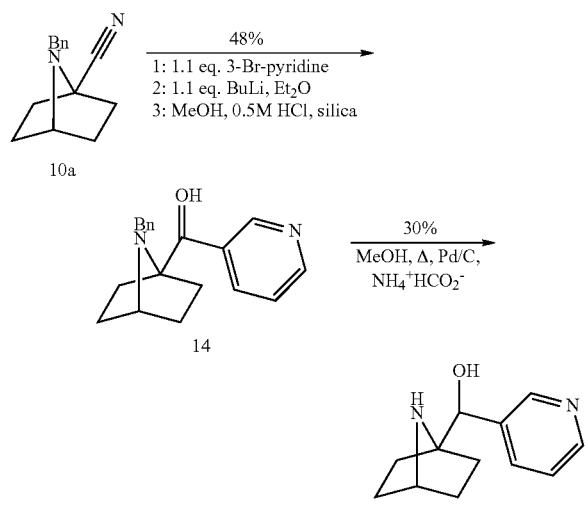

Details of these syntheses are as follows:

Synthesis of Compound 14

In a dry 50 ml flask 1.05 g (5 mmole, 1 eq.) 7-benzyl-7-azabicyclo[2.2.1]heptyl-1-carbonitrile 10a and 0.87 g (5.5 mmole, 1.1 eq.) 3-bromopyridine were dissolved in 25 ml dry diethyl ether. The flask was placed under N$_2$-atmosphere and cooled to −40° C. Using a syringe pump 2.2 ml of a 2.5M solution (5.5 mmole, 1.1 eq.) BuLi was added over a period of 30 minutes. The reaction mixture was stirred for one hour at −40° C. and then allowed to slowly heat up to 20° C. Methanol was added in order to neutralise the excess BuLi and the volatile components were evaporated. The reaction mixture was re-dissolved in 25 ml of a 1:1 mixture of methanol and 0.5M HCl. 0.5 g of silica gel was added and the mixture was stirred for 15 hours at room temperature. The pH was adjusted to 8 by adding a concentrated NaHCO$_3$ solution. Compound 14 was extracted three times by means of dichloromethane and the combined organic phases were dried over MgSO$_4$. After filtration of the solids and evaporation of the volatile components, compound 14 (yield 48%) was purified by means of column chromatography and was characterised by spectral data as follows:

$^1$H-NMR (300 MHz, CDCl$_3$) (ppm): 1.48 (2H, dxdxd, J=11.7 Hz, $J_2$=9.2 Hz, $J_3$=4.0 Hz, 2×CHCH$_{exo}$H$_{endo}$ of 2×C$_q$CH$_a$H$_b$ ring); 1.69-1.87 (2H, br. s, 2×CHCH$_{exo}$H$_{endo}$ of 2×C$_q$CH$_a$H$_b$ ring); 1.92-2.06 (2H, m, 2×CHCH$_{exo}$H$_{endo}$); 2.26-2.40 (1H, m, 2×CHCH$_{exo}$H$_{endo}$ of C$_q$CH$_a$H$_b$ ring); 3.40 (2H, s, NCH$_2$Ph); 3.41 (1H, t, J=4.5 Hz, CH$_2$CHCH$_2$); 7.18-7.30 (5H, m, 5×CH Ph.); 7.40 (1H, dxdxd, $J_1$=8.0 Hz, $J_2$=5.0 Hz, $J_3$=0.7 Hz, NCHCH pyr.); 8.75 (1H, dxd, $J_1$=5.0 Hz, $J_2$=2.0 Hz, NCHCH pyr.); 8.79 (1H, dxt, $J_1$=8.0 Hz, $J_2$=2.0 Hz, C$_q$CHCH pyr.) and 9.89 (1H, dxd, $J_1$=2.0 Hz, $J_2$=0.7 Hz, C$_q$CHN pyr.);

$^{13}$C-NMR (75 MHz, CDCl$_3$) (ppm): 28.5-30.6 (4×CH$_2$ ring); 50.16 (NCH$_2$Ph); 59.63 (CH$_2$CHCH$_2$); 77.16 (CDCl$_3$); 77.59 (CH$_2$C$_q$CH$_2$); 123.42 (NCHCH pyr.); 127.16 (1×CH Ph.); 128.40 (2×CH Ph.); 128.61 (2×CH Ph.); 130.70 (C$_q$ pyr.); 137.24 (C$_q$CHCH); 139.15 (C$_q$ Ph.); 151.77 (C$_q$CHN pyr.); 153.36 (NCHCH pyr.) and 200.71 (CO);

IR (cm$^{-1}$): 1675 (C=O); and

MS$^{ES}$ m/z (%): 293.2 (M+H$^+$, 100).

Synthesis of Compound 15

In a 50 ml flask 0.10 g (0.34 mmole, 1 eq.) 7-benzyl-7-azabicyclo[2.2.1]hept-1-yl)(pyridin-3-yl)methanone 14 and 0.09 g (1.37 mmole, 4 eq.) ammonium formate were dissolved in 20 ml methanol. To this solution 0.05 g (5% Pd) Pd/C was added and the suspension was refluxed 4 hours. The Pd/C catalyst was filtered off and methanol evaporated. 5 ml dichloromethane was added and the excess ammonium formate was filtered off. After evaporation of dichloromethane, compound 15 (yield 30%) was further purified by crystallisation from diethyl ether and was characterised by spectral data as follows:

$^1$H-NMR (300 MHz, CDCl$_3$) (ppm): 1.07 (1H, dxdxd, $J_1$=11.9 Hz, $J_2$=9.2 Hz, $J_3$=4.3 Hz, C$_q$C$_a$H$_a$H$_b$ ring); 1.13-1.25 (1H, m, C$_q$C$_b$H$_a$H$_b$ ring); 1.39-1.51 (2H, m, 2×CHCH$_{exo}$H$_{endo}$ ring); 1.57 (1H, txt, $J_1$=11.8 Hz, $J_2$=3.7 Hz, C$_q$C$_b$H$_a$H$_b$ ring); 1.64-1.82 (2H, m, 2×CHC H$_{exo}$H$_{endo}$ ring); 1.89 (1H, txt, $J_1$=11.9 Hz, $J_2$=3.9 Hz, C$_q$C$_a$H$_a$H$_b$ ring); 3.62 (1H, t, J=4.5 Hz, CHCH$_2$ ring); 3.79 (2H, br. s, OH+NH); 5.06 (1H, s, CHOH); 7.26 (1H, dxd, $J_1$=7.9 Hz, $J_2$=4.7 Hz, NCHCH pyr.); 7.76 (1H, dxt, $J_1$=7.9 Hz, $J_2$=1.7 Hz, $C_q$CHCH pyr.); 8.50 (1H, dxd, $J_1$=4.7 Hz, $J_2$=1.7 Hz, NCHCH pyr.) and 8.59 (1H, d, J=1.7 Hz, NCHC$_q$ pyr.);

$^{13}$C-NMR (75 MHz, CDCl$_3$) (ppm): 27.93 (C$_q$C$_a$H$_2$ ring); 31.08 (1×CHCH$_2$ ring); 31.45 (1×CHCH$_2$ ring); 32.73 (C$_q$C$_b$H$_2$ ring); 56.78 (CHCH$_2$ ring); 72.01 (C$_q$CH$_2$ ring); 73.31 (CHOH); 77.33 (CDCl$_3$); 123.25 (NCHCH pyr.); 134.44 (C$_q$CHCH pyr.); 137.70 (C$_q$ pyr.); 148.35 (NCHC$_q$ pyr.) and 148.86 (NCHCH pyr.);

IR (cm$^{-1}$): 3436 (OH or NH) and 3234 (OH of NH);

MS$^{ES}$ m/z (%): 205.2 (M+H$^+$, 100); and

Melting point 139.5° C.

EXAMPLE 5

Preparation of 7-benzyl-7-azabicyclo[2.2.1]hept-1-ylmethyl)-pyridin-2-yl-amine

In a different approach, 7-azabicyclo[2.2.1]heptane-1-carbonitrile 10a was converted to compounds 16 and 17 according to scheme 5.

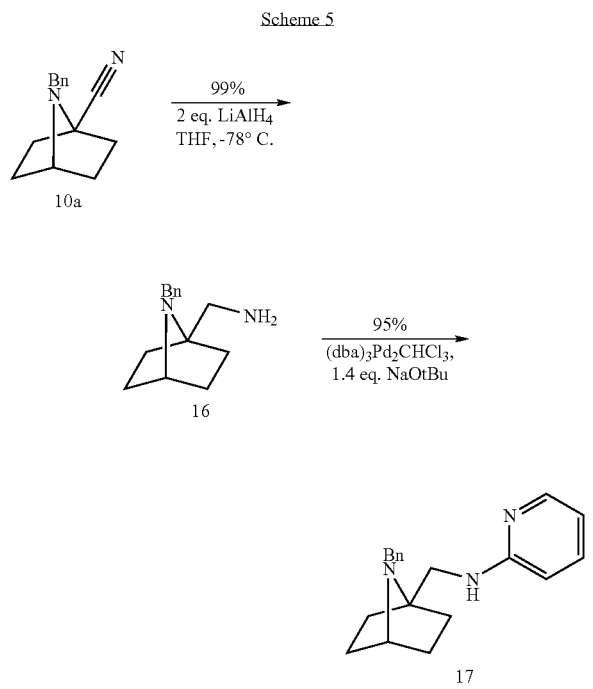

Reduction of compound 10a to 16 by means of LiAlH$_4$ was performed quantitatively. Next, the pyridyl group was introduced onto the side chain of the 7-azabicyclo[2.2.1]hept-1-yl ring by means of a Pd catalysed cross-coupling reaction. Standard Buchwald conditions were used to test different ligands: Binap, dppp and di-tert-butyl-{1-[2-(dicyclohexylphosphanyl) ferrocenyl]ethyl}phosphine (dfep) provided conversions of 48%, 12% and 10% respectively. Using the more efficient ligand Binap, several pyridyl groups and operating conditions were tested, as shown in table 1 indicating the resulting yields. The best results were obtained using 1 eq. 2-bromopyridine, 1.4 eq. sodium tert-butoxide and 4 mole % of a (dba)$_3$Pd$_2$CHCl$_3$ catalyst.

TABLE 1

| | 2-chloro-pyridine | 2-bromopyridine | | |
|---|---|---|---|---|
| | 1.2 equiv. amine | 1.2 equiv. amine | 1 equiv. amine | 0.8 equiv. amine |
| 2% catalyst | 56% | 59% | 91% | 85% |
| 4% catalyst | 62% | 77% | 95% | N/A$^a$ |

$^a$N/A: not available

Ligand requirements for this reaction proved to be highly dependent upon the substrate. Using 2-bromopyridine the ligand of choice was Binap, giving a conversion of 95% over 2 days. Using 3-bromopyridine and dfep as a ligand, a 55% conversion was obtained and the secondary amine 18 (shown in scheme 6 below) was isolated in 47% yield after column chromatography.

Details of these syntheses are as follows:

Synthesis of Compound 16

In a dry 50 ml flask 0.72 g LiAlH$_4$ (18.8 mmole, 2 eq.) was suspended in 10 ml dry THF. The flask was placed under inert N$_2$-atmosphere and cooled to −78° C. To this suspension 2 g 7-benzyl-7-azabicyclo[2.2.1]heptyl-1-carbonitrile 10a (9.4 mmole, 1 eq.) dissolved in 30 ml dry THF was added dropwise. The cooling equipment was removed and the reaction mixture was allowed to heat up to room temperature. The reaction mixture was stirred overnight. After cooling to 0° C., water was carefully added to neutralise the excess LiAlH$_4$. The reaction mixture was dried by adding. MgSO$_4$ and, after filtration of the solids and removal of the volatile components, 7-benzyl-7-azabicyclo[2.2.1]hept-1-yl)-methylamine 16 was obtained (yield 99%) as a slightly yellow solid and was characterised by spectral data as follows:

$^1$H-NMR (300 MHz, CDCl$_3$) (ppm): 1.31-1.43 (4H, m, 2×CH$_a$H$_b$CH, 2×CH$_a$H$_b$C$_q$); 1.50-1.60 (2H, br. s, NH$_2$); 1.65-1.87 (4H, m, 2×CH$_a$H$_b$CH, 2×CH$_a$H$_b$C$_q$); 2.90 (2H, s, CH$_2$NH$_2$); 3.18 (1H, t, J=4.4 Hz, CH$_2$CHCH$_2$); 3.42 (2H, s, NCH$_2$Ph) and 7.19-7.42 (5H, m, 5×CH, Ph.);

$^{13}$C-NMR (75 MHz, CDCl$_3$) (ppm): 28.29 (2×CH$_2$CH); 31.35 (2×CH$_2$C$_q$); 43.51 (CH$_2$NH$_2$); 49.11 (NCH$_2$Ph); 59.77 (CH$_2$CHCH$_2$); 69.36 (CH$_2$C$_q$CH$_2$); 126.80 (CH, Ph.); 128.28 (2×CH, Ph.); 128.72 (2×CH, Ph.) and 140.35 (C$_q$, Ph.);

IR (cm$^{-1}$): 3368 (NH$_2$);

MS$^{ES}$ m/z (%): 217 (M+H$^+$, 100); and

Melting point 71-72.7° C.

Synthesis of Compound 17

In a dry tube 0.66 g (3 mmole, 1 eq.) 7-benzyl-7-azabicyclo[2.2.1]hept-1-yl)-methylamine 16, 0.47 g (3 mmole, 1 eq.) 2-bromopyridine and 0.41 g (4.2 mmole, 1.4 eq.) sodium tert-butoxide were dissolved in 25 ml dry toluene. The tube was flushed with argon and 124 mg (0.12 mmole, 8 mole % Pd) of a catalyst (dba)$_3$Pd$_2$CHCl$_3$ and 149 mg (0.24 mmole, 8 mole %) Binap were added. The tube was flushed a second time with argon, closed and heated to 70° C. Fifty hours later the reaction was ended by filtration of the Pd-catalyst. Toluene was removed under vacuum and the residue was re-dissolved in dichloromethane. A saturated NaHCO$_3$ solution was added and extracted twice with dichloromethane. The combined organic phases were dried over MgSO$_4$ and evaporated. Compound 15 was obtained as a orange oil in 95% yield and was characterised by spectral data as follows:

$^1$H-NMR (300 MHz, CDCl$_3$) (ppm): 1.30-1.47 (4H, m, 2×CH$_a$H$_b$CH, 2×CH$_a$H$_b$C$_q$); 1.72-1.89 (4H, m, 2×CH$_a$H$_b$CH, 2×CH$_a$H$_b$C$_q$); 3.19 (1H, br s, CH$_2$CHCH$_2$); 3.40 (2H, s, NCH$_2$Ph); 3.49 (2H, d, J=4.4 Hz, C$_q$CH$_2$NH); 4.89 (1H, ~t, J=4.4 Hz, NH); 6.30 (1H, d, J=8.3 Hz, C$_q$CH pyr.); 6.49 (1H, dxdxd, J$_1$=7.0 Hz, J$_2$=5.0 Hz, J$_3$=0.8 Hz, NCHCH pyr.); 7.16-7.38 (6H, m, 5×CH Ph, C$_q$CHCH pyr.) and 8.06 (1H, m, NCH pyr.);

$^{13}$C-NMR (75 MHz, CDCl$_3$) (ppm): 28.44 (2×CH$_2$ ring); 32.03 (2×CH$_2$ ring); 43.02 (CH$_2$NH); 48.84 (NCH$_2$Ph); 59.54 (CH$_2$CHCH$_2$); 67.54 (CH$_2$C$_q$CH$_2$); 107.48 (Cq CH pyr.); 112.52 (NCHCH pyr.); 126.89 (CH Ph.); 128.35 (2×CH Ph.); 128.72 (2×CH Ph.); 137.19 (C$_q$CH CH pyr.); 140.35 (C$_q$ Ph.); 148.09 (NCH pyr.) and 158.93 (C$_q$ pyr.);

IR (cm$^{-1}$): 3375 (NH); and

MS$^{ES}$ m/z (%): 294 (M+H$^+$, 100).

CH Ph.); 135.71 (NCHC$_q$ pyr.); 138.37 (NCHCH pyr.); 140.19 (C$_q$ Ph.) and 144.61 (C$_q$ pyr.);

IR (cm$^{-1}$): 3372 (NH);

MS$^{ES}$ m/z (%): 294 (M+H$^+$, 100); and

Melting point 66.8-68.6° C.

EXAMPLE 6

Preparation of 7-azabicyclo[2.2.1]hept-1-ylmethyl)-pyridinylamines

Removal of the protective benzyl group was performed by refluxing in methanol, using ammonium formate as reducing agent, as shown in scheme 6 below. Compound 5 was obtained after 1 hour of reflux, while for compound 19 a period of 2 hours was necessary to drive the reaction to completion. The low yield for compound 19 may be attributed to a troublesome purification. Compound 5 was easily separated from the excess ammonium formate by dissolution in dry diethyl ether. Compound 19 however does not dissolve in diethyl ether. Eventually, separation of the ammonium salts was obtained by a temperature controlled selective crystallisation from hexane.

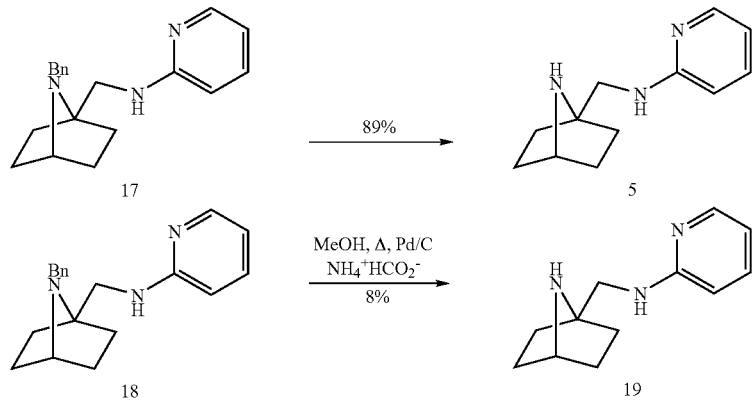

Synthesis of Compound 18

Synthesis proceeded by analogy to compound 17, except that t-butyl-{1-[2-(dicyclohexylphosphanyl)ferrocenyl]ethyl}phosphine (dfep) was used as a ligand and 3-bromopyridine used instead of 2-bromopyridine. Purification was performed by means of column chromatography. Compound (yield 47%) was characterised by spectral data as follows:

$^1$H-NMR (300 MHz, CDCl$_3$) (ppm): 1.36-1.50 (4H, m, 2×CH$_{exo}$H$_{endo}$CH, 2×CH$_a$H$_b$C$_q$); 1.79-1.90 (4H, m, 2×CH$_{exo}$H$_{endo}$CH, 2×CH$_a$H$_b$C$_q$); 3.21-3.27 (3H, m, CH$_2$CHCH$_2$, CH$_2$NH); 3.38 (2H, s, NCH$_2$Ph); 4.17 (1H, ~t, J=4.1 Hz, NH); 6.76 (1H, dxdxd, J$_1$=8.3 Hz, J$_2$=2.8 Hz, J$_3$=1.1 Hz, C$_q$CHCH pyr.); 7.02 (1H, dxd, J$_1$=8.3 Hz, J$_2$=4.7 Hz, C$_q$CHCH pyr.); 7.15-7.37 (5H, m, 5×CH Ph); 7.90 (1H, dxd, J$_1$=4.7 Hz, J$_2$=1.1 Hz, NCHCH pyr.) and 7.93 (1H, d, J=2.8 Hz, NCHC$_q$ pyr.);

$^{13}$C-NMR (75 MHz, CDCl$_3$) (ppm): 28.48 (2×CH$_2$ ring); 32.07 (2×CH$_2$ ring); 44.62 (CH$_2$NH); 48.94 (NCH$_2$Ph); 60.09 (CH$_2$CHCH$_2$); 67.65 (CH$_2$C$_q$CH$_2$); 77.13 ( CDCl$_3$); 118.25 (C$_q$CHCH pyr.); 123.67 (C$_q$CHCH pyr.); 127.00 (CH Ph.); 128.43 (2×CH Ph.); 128.58 (2×

Details of these syntheses are as follows:

Synthesis of Compound 5

In a 50 ml flask 0.76 g (2.3 mmole, 1 eq.) 7-benzyl-7-azabicyclo[2.2.1]hept-1-ylmethyl)-pyridin-2-yl-amine 17 and 0.67 g (10.6 mmole, 3 eq.) ammonium formate were dissolved in 40 ml methanol. To this solution 0.38 g of a Pd/C catalyst (5% Pd) was added. The suspension was refluxed during one hour, after which the Pd/C catalyst was filtered off and the methanol evaporated. Compound 5 (89%) was extracted from the remaining solids by means of dry diethyl ether and was characterised by spectral data as follows:

$^1$H-NMR (300 MHz, CDCl$_3$) (ppm): 1.42-1.62 (6H, m, 4×CH$_{exo}$H$_{endo}$ ring, 2×C$_q$CH$_{exo}$H$_{endo}$ ring); 1.66-1.80 (2H, m, 2×CHCH$_{exo}$H$_{endo}$); 1.86-1.97 (1H, br. s, CHN H); 3.64 (1H, t, J=4.5 Hz, CH$_2$CHCH$_2$); 3.66 (2H, d, J=5.8 Hz, NCH$_2$); 4.84-4.95 (1H, m, CH$_2$NH); 6.46 (1H, dxt, J$_1$=8.4 Hz, J$_2$=0.8 Hz, C$_q$CHCH pyr.); 6.55 (1H, dxdxd, J$_1$=7.0 Hz, J$_2$=5.0 Hz, J$_3$=0.8 Hz, NCHCH pyr.); 7.39 (1H, dxdxd, J$_1$=8.4 Hz, J$_2$=7.0 Hz, J$_3$=1.9 Hz, C$_q$CHCH pyr.) and 8.07 (1H, dxdxd, J$_1$=5.0 Hz, J$_2$=1.9 Hz, J$_3$=0.8 Hz, NCHCH pyr.);

$^{13}$C-NMR (75 MHz, CDCl$_3$) (ppm): 31.75 (2×CH$\underline{C}$H$_2$ ring); 32.94 (2×C$_q$$\underline{C}$H$_2$ ring); 45.46 ($\underline{C}$H$_2$NH); 57.07 ($\underline{C}$H$_2$CHCH$_2$); 67.30 (CH$_2$$\underline{C}_q$CH$_2$); 77.13 (CDCl$_3$); 107.45 (C$_q$$\underline{C}$HCH pyr.); 112.78 (NCH$\underline{C}$H pyr.); 137.39 (C$_q$$\underline{C}$HCH pyr.); 148.08 (N$\underline{C}$HCH pyr.) and 159.12 ($\underline{C}_q$ pyr.);

IR (cm$^{-1}$): 3410 (NH) and 3263 (NH);
MS$^{ES}$ m/z (%): 204 (M+H$^+$, 100); and
Melting point: 73.8-74.2° C.

Synthesis of Compound 19

0.18 g (0.61 mmole, 1 eq.) 7-benzyl-7-azabicyclo[2.2.1]hept-1-ylmethyl)pyridin-3-ylamine 18 and 0.15 g (2.45 mmole, 4 eq.) ammonium formate were dissolved in 20 ml methanol. To this solution 0.09 g of a Pd/C catalyst (5% Pd) was added. The suspension was refluxed during 2 hours after which the Pd/C catalyst was removed by filtration and methanol was evaporated. The solid residue was treated with boiling hexane, decanted and cooled to −20° C. Crystals of compound 19 (formed in 8% yield) were characterised by spectral data as follows:

$^1$H-NMR (300 MHz, CDCl$_3$) (ppm): 1.45-1.68 (6H, m, 2×CHCH$_{exo}$$\underline{H}_{endo}$, 2×C$_q$C$\underline{H}_2$); 1.73-1.96 (3H, m, 2×CHCH$_{exo}$$\underline{H}_{endo}$, CHN$\underline{H}$); 3.44 (2H, d, J=4.1 Hz, C$\underline{H}_2$NH); 3.68 (1H, t, J=4.5 Hz, CH$_2$C$\underline{H}$CH$_2$); 4.30 (1H, br. s, CH$_2$N$\underline{H}$); 6.92 (1H, dxdxd, J$_1$=8.3 Hz, J$_2$=2.7 Hz, J$_3$=1.1 Hz, C$_q$$\underline{C}$HCH pyr.); 7.07 (1H, dxd, J$_1$=8.3 Hz, J$_2$=4.7 Hz, C$_q$CHC$\underline{H}$ pyr.); 7.94 (1H, dxd, J$_1$=1.1 Hz, J$_2$=4.7 Hz, NCHC$\underline{H}$ pyr.) and 8.06 (1H, d, J=2.7 Hz, NC$\underline{H}$C$_q$ pyr.);

$^{13}$C-NMR (75 MHz, CDCl$_3$) □ (ppm): 31.57 (2×CH$\underline{C}$H$_2$); 32.99 (2×C$_q$$\underline{C}$H$_2$); 47.02 ($\underline{C}$H$_2$NH); 57.20 (CH$_2$$\underline{C}$HCH$_2$); 67.40 (CH$_2$$\underline{C}_q$CH$_2$); 118.47 (C$_q$$\underline{C}$HCH pyr.); 123.79 (C$_q$CH$\underline{C}$H pyr.); 135.99 (N$\underline{C}$HC$_q$ pyr.); 138.70 (N$\underline{C}$HCH pyr.) and 144.71 (C$_q$ pyr.);

IR (cm$^{-1}$): 3435 (NH); and
MS$^{ES}$ m/z (%): 204.2 (M+H$^+$, 100).

The invention claimed is:

1. A 1-substituted-7-azabicyclo[2.2.1]heptyl derivative represented by the structural formula (I):

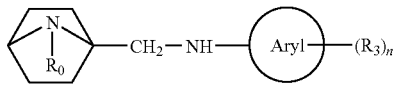

or the structural formula (II):

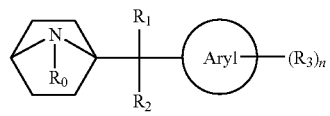

wherein:
R$_0$ is selected from the group consisting of hydrogen, benzyl, naphthylmethyl, C$_{3-4}$ alkenyl and C$_{1-8}$ alkyl, wherein said benzyl is optionally substituted with one to three substituents independently selected from the group consisting of halogen, C$_{1-4}$ alkyl, C$_{1-4}$ alkoxy, trifluoromethyl, trifluoromethoxy, dimethylaminoethoxy, dimethylaminopropoxy, morpholinoethoxy, phenoxy, phenoxymethyl, heteroaryl and heteroaryl-methyl;

R$_1$ is hydrogen and R$_2$ is hydroxyl, or R$_1$ in combination with R$_2$ is oxo or imino;

R$_3$ is a substituent selected from the group consisting of fluoro, chloro, bromo, C$_{1-4}$ alkyl, C$_{1-4}$ alkoxy, C$_{1-4}$ alkylthio, cyano, phenyl, trifluoromethyl, trifluoromethoxy, amino, dimethylamino and tert-butylcarboxylate; and n is 0, 1 or 2; and Aryl is an arylene or heteroarylene divalent group, or a pharmaceutically acceptable salt thereof, or a stereochemically isomeric form thereof, or a solvate thereof.

2. The 1-substituted-7-azabicyclo[2.2.1]heptyl derivative according to claim 1, wherein Aryl is phenylene, or a pharmaceutically acceptable salt thereof, or a stereochemically isomeric form thereof, or a solvate thereof.

3. The 1-substituted-7-azabicyclo[2.2.1]heptyl derivative according to claim 2, wherein n is 1.

4. The 1-substituted-7-azabicyclo[2.2.1]heptyl derivative according to claim 1, wherein Aryl is pyrid-3-ylene or pyrid-2-ylene, or a pharmaceutically acceptable salt thereof, or a stereochemically isomeric form thereof, or a solvate thereof.

5. The 1-substituted-7-azabicyclo[2.2.1]heptyl derivative according to claim 4, wherein n is 1.

6. A method for producing a 1-substituted-7-azabicyclo[2.2.1]heptyl derivative according to claim 1 and being represented by the structural formula (II) wherein R$_1$ is hydrogen and R$_2$ is hydroxyl, comprising:
reacting a 1-formyl-7-R$_0$-substituted-7-azabicyclo[2.2.1]-heptane, wherein R$_0$ is as defined in claim 1, with an optionally substituted aryl iodide or aryl bromide represented by the structural formula Y-Aryl-(R$_3$)$_n$ wherein Y is iodo or bromo, Aryl, n and R$_3$ are as defined in claim 1.

7. The method according to claim 6, further comprising the step of cleaving off the N-protecting R$_0$ substituent.

8. A method for producing a 1-substituted-7-azabicyclo[2.2.1]heptyl derivative according to claim 1 and being represented by the structural formula (II) wherein R$_1$ in combination with R$_2$ is oxo, comprising:
reacting a 1-cyano-7-R$_0$-substituted-7-azabicyclo[2.2.1]-heptane, wherein R$_0$ is as defined in claim 1, with an optionally substituted aryl iodide or aryl bromide represented by the structural formula Y-Aryl-(R$_3$)$_n$ wherein Y is iodo or bromo, Aryl, n and R$_3$ are as defined in claim 1.

9. The method according to claim 8, further comprising the step of cleaving off the N-protecting R$_0$ substituent.

10. A method for producing a 1-substituted-7-azabicyclo[2.2.1]heptyl derivative according to claim 1 and being represented by the structural formula (I) comprising:
submitting a 1-aminomethyl-7-R$_0$-substituted-7-azabicyclo[2.2.1]-heptane, wherein R$_0$ is as defined in claim 1, to a reaction step with an optionally substituted aryl iodide or aryl bromide represented by the structural formula Y-Aryl-(R$_3$)$_n$ wherein Y is iodo or bromo, Aryl, n and R$_3$ are as defined in claim 1.

11. The method according to claim 10, wherein said reaction is a Buchwald-Hartwig cross-coupling reaction.

12. The method according to claim 10, wherein said reaction is performed in the presence of a palladium complex catalyst.

13. The method according to claim 10, further comprising the step of cleaving off the N-protecting R$_0$ substituent.

14. A pharmaceutical composition comprising a therapeutically effective amount of a 1-substituted-7-azabicyclo[2.2.1]heptyl derivative according to claim 1.

15. The pharmaceutical composition according to claim 14, further comprising one or more pharmaceutically acceptable excipients.

16. A 1-formyl-7-$R_0$-substituted-7-azabicyclo[2.2.1]-heptane or 1-cyano-7-$R_0$-substituted-7-azabicyclo[2.2.1]-heptane, wherein $R_0$ is selected from the group consisting of hydrogen, benzyl, naphthylmethyl, $C_{3-4}$ alkenyl and $C_{1-8}$ alkyl, wherein said benzyl is optionally substituted with one to three substituents independently selected from the group consisting of halogen, $C_{1-8}$ alkyl, $C_{1-8}$ alkoxy, trifluoromethyl, trifluoromethoxy, dimethylaminoethoxy, dimethylaminopropoxy, morpholinoethoxy, phenoxy, phenoxymethyl, heteroaryl and heteroaryl-methyl.

17. A method for producing a 1-cyano-7-$R_0$-substituted-7-azabicyclo[2.2.1]-heptane comprising:

reacting 4-methanesulfonyl-cyclohexanone with a molar excess of a primary amine $R_0NH_2$, wherein $R_0$ is selected from the group consisting of benzyl, naphthylmethyl, $C_{3-4}$ alkenyl and $C_{1-8}$ alkyl, wherein said benzyl is optionally substituted with 1 to 3 substituents independently selected from the group consisting of halogen, $C_{1-4}$ alkyl, $C_{1-4}$ alkoxy, trifluoromethyl, trifluoromethoxy, dimethylaminoethoxy, dimethylaminopropoxy, morpholinoethoxy, phenoxy, phenoxymethyl, heteroaryl and heteroaryl-methyl.

18. The 1-substituted-7-azabicyclo[2.2.1]heptyl derivative according to claim 4, wherein n is 0.

19. The 1-substituted-7-azabicyclo[2.2.1]heptyl derivative according to claim 4, wherein $R_0$ is hydrogen.

20. The 1-substituted-7-azabicyclo[2.2.1]heptyl derivative according to claim 4, wherein n is 0 and $R_0$ is hydrogen.

21. The 1-substituted-7-azabicyclo[2.2.1]heptyl derivative according to claim 4, being represented by the structural formula (II) wherein $R_1$ is hydrogen and $R_2$ is hydroxyl.

22. The 1-substituted-7-azabicyclo[2.2.1]heptyl derivative according to claim 4, being represented by the structural formula (II) wherein $R_1$ is hydrogen, $R_2$ is hydroxyl and $R_0$ is hydrogen.

23. The 1-substituted-7-azabicyclo[2.2.1]heptyl derivative according to claim 4, being represented by the structural formula (II) wherein $R_1$ is hydrogen, $R_2$ is hydroxyl, $R_0$ is hydrogen, and n is 0.

24. The 1-substituted-7-azabicyclo[2.2.1]heptyl derivative according to claim 4, being represented by the structural formula (I) wherein n is 0 and $R_0$ is hydrogen.

25. A pharmaceutical composition comprising a therapeutically effective amount of a 1-substituted-7-azabicyclo[2.2.1]heptyl derivative according to claim 4.

26. A pharmaceutical composition comprising a therapeutically effective amount of a 1-substituted-7-azabicyclo[2.2.1]heptyl derivative according to claim 18.

27. A pharmaceutical composition comprising a therapeutically effective amount of a 1-substituted-7-azabicyclo[2.2.1]heptyl derivative according to claim 19.

28. A pharmaceutical composition comprising a therapeutically effective amount of a 1-substituted-7-azabicyclo[2.2.1]heptyl derivative according to claim 20.

29. A pharmaceutical composition comprising a therapeutically effective amount of a 1-substituted-7-azabicyclo[2.2.1]heptyl derivative according to claim 21.

30. A pharmaceutical composition comprising a therapeutically effective amount of a 1-substituted-7-azabicyclo[2.2.1]heptyl derivative according to claim 22.

31. A pharmaceutical composition comprising a therapeutically effective amount of a 1-substituted-7-azabicyclo[2.2.1]heptyl derivative according to claim 23.

32. A pharmaceutical composition comprising a therapeutically effective amount of a 1-substituted-7-azabicyclo[2.2.1]heptyl derivative according to claim 24.

* * * * *